United States Patent
Cleveland et al.

(10) Patent No.: US 10,806,743 B1
(45) Date of Patent: Oct. 20, 2020

(54) METHOD OF ADMINISTERING LACTITOL TO REDUCE PLASMA CONCENTRATION OF LACTITOL

(71) Applicant: Braintree Laboratories, Inc., Braintree, MA (US)

(72) Inventors: Mark vB Cleveland, Norwell, MA (US); Robert M Raleigh, Pembroke, MA (US); Russell W Pelham, Duxbury, MA (US)

(*) Notice: Subject to any disclaimer, the term of this patent is extended or adjusted under 35 U.S.C. 154(b) by 0 days.

(21) Appl. No.: 15/594,109

(22) Filed: May 12, 2017

(51) Int. Cl.
| | |
|---|---|
| A61K 31/7032 | (2006.01) |
| A61K 9/00 | (2006.01) |
| A61K 9/20 | (2006.01) |
| A23L 2/52 | (2006.01) |
| A23L 33/00 | (2016.01) |
| A61K 31/352 | (2006.01) |

(52) U.S. Cl.
CPC ............ *A61K 31/7032* (2013.01); *A23L 2/52* (2013.01); *A23L 33/30* (2016.08); *A61K 9/0095* (2013.01); *A61K 9/20* (2013.01); *A61K 31/352* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,814,195 A * | 3/1989 | Yokoyama | A23L 33/21 426/633 |
| 4,973,486 A | 11/1990 | Matsumoto | |
| 5,160,546 A | 11/1992 | Kawashima | |
| 5,516,763 A | 5/1996 | Heikkila | |
| 5,672,589 A | 9/1997 | Heikkila | |
| 5,726,303 A | 3/1998 | Wijnman | |
| 5,989,352 A | 11/1999 | Caboche | |
| 6,090,429 A | 7/2000 | Wilson | |
| 6,251,875 B1 | 6/2001 | Saunders | |
| 6,350,469 B1 * | 2/2002 | Daggy | A61K 9/0056 424/464 |
| 6,384,020 B1 | 5/2002 | Flanner | |
| 6,395,893 B1 | 5/2002 | Heikkila | |
| 6,444,250 B1 | 9/2002 | Blankers | |
| 2008/0044493 A1 * | 2/2008 | Sato | A61K 31/047 424/683 |
| 2008/0050492 A1 | 2/2008 | Beutler | |

FOREIGN PATENT DOCUMENTS

| | | |
|---|---|---|
| EP | 0218324 A1 | 4/1987 |
| EP | 0284747 A3 | 7/1990 |
| EP | 0906109 B1 | 6/2001 |
| EP | 0844881 B1 | 10/2002 |
| EP | 0938301 B1 | 12/2002 |

OTHER PUBLICATIONS

Faruqui, A. A., & Joshi, C. (2012). Lactitol: a review of its use in the treatment of constipation. Int J Recent Adv Pharm Res, 2(1), 1-5. (Year: 2012).*

Ambizas, E. M., & Ginzburg, R. (2007). Lubiprostone: a chloride channel activator for treatment of chronic constipation. Annals of Pharmacotherapy, 41(6), 957-964. (Year: 2007).*

Oku, T., & Nakamura, S. (2007). Threshold for transitory diarrhea induced by ingestion of xylitol and lactitol in young male and female adults. Journal of nutritional science and vitaminology, 53(1), 13-20. (Year: 2007).*

Hou, Y. Q. et al. Effects of Lactitol and Tributyrin on Growth Performance, Small Intestinal Morphology and Enzyme Activity in Weaned Pigs. Asian-Aust. J. Anim. Sci. Oct. 2006, 19(10):1470-1477.

Patil, D. H. et al. Comparative modes of action of lactitol and lactulose in the treatment of hepatic encephalopathy. Gut, 1987, 28:255-259.

Lanthier, P. L. and Morgan M. Y. Lactitol in the treatment of chronic hepatic encephalopathy: an open comparison with lactulose. Gut, 1985, 26:415-420.

Grimble, G. K. et al. Assimilation of lactitol, an 'unabsorbed' disaccharide in the normal human colon. Gut, 1988, 29:1666-1671.

Makelainen, H. et al. Xylo-oligosaccharides and lactitol promote the growth of Bifidobacterium lactis and *Lactobacillus* species in pure cultures. Beneficial Microbes, Jun. 2010, 1(2):139-148.

Makivuokko, H. et al. Synbiotic effects of lactitol and Lactobacillus acidophilus NCFM™ in a semicontinuous colon fermentation model. Beneficial Microbes, Jun. 2010, 1(2):131-137.

Peuranen. et al. Combination of polydextrose and lactitol affects microbial ecosystem and immune responses in rat gastrointestinal tract. British J. Nut. 2004, 91:905-914.

Nilsson, U. and Jagerstad, M. Hydrolysis of lactitol, maltitol and Palatinit by human intestinal biopsies. British J. Nut. 1987, 58:199-206.

Ouwehand, A. C. et al. Influence of a combination of Lactobacillus acidophilus NCFM and lactitol on healthy elderly: intestinal and immune parameters. British j. Nut. 2009, 101:367-375.

Yanahira, S. et al. Effects of Lactitol-Oligosaccharides on Calcium and Magnesium Absorption in Rats. J. Nutr. Sci. Vitaminol. 1997, 43:123-132.

Patil, D. H. et al. Lactitol, a new hydrogenated lactose derivative: intestinal absorption and laxative threshold in normal human subjects. British J. Nut. 1987, 57:195-199.

Yanahira, S. et al. Effects of Lactitol-Oligosaccharides on the Intestinal Microflora in Rats. J. Nutr. Sci. Vitaminol. 1995, 41:83-94.

Hiele, M. et al. Metabolism of erythritol in humans : comparison with glucose and lactitol. British J. Nut. 1993, 69:169-176.

* cited by examiner

*Primary Examiner* — Dale R Miller

(57) ABSTRACT

Disclosed herein are formulations comprising lactitol for the treatment of chronic idiopathic constipation. As disclosed herein, the formulations are administered after or during a meal to improve the pharmacokinetics of the formulation. In particular, administration of the formulation after or during a meal decreases the absorption of lactitol and reduces the AUC.

21 Claims, 1 Drawing Sheet

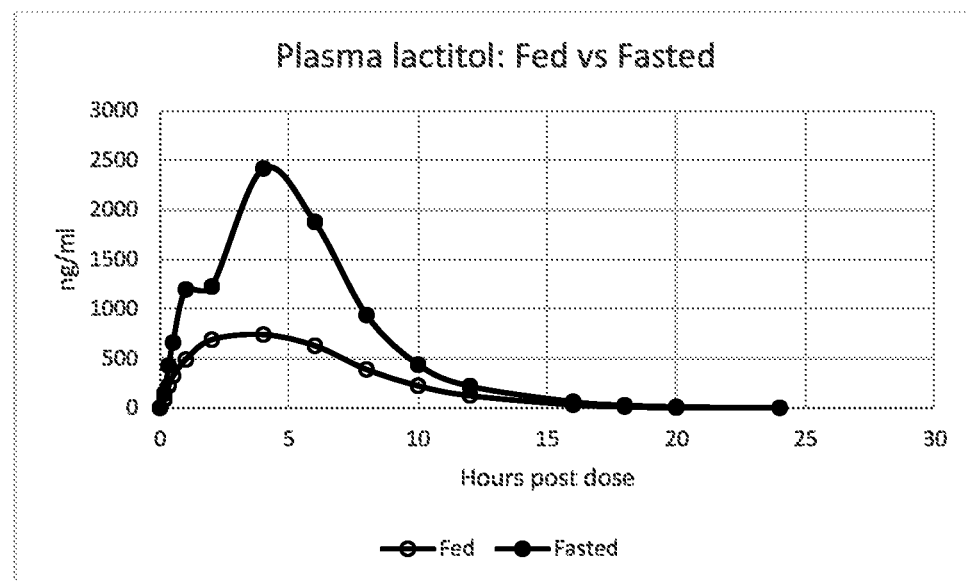

METHOD OF ADMINISTERING LACTITOL TO REDUCE PLASMA CONCENTRATION OF LACTITOL

FIELD

This disclosure relates generally to the field of medicine and particularly to treatment of gastrointestinal conditions.

BACKGROUND

Chronic idiopathic constipation ("CIC") is a condition that affects between 4% and 20% of the population (see Suares and Ford (2011) *Aliment Pharmacol Ther.* 33(8):895-901). The disorder is defined as infrequent and difficult passage of stools in the absence of any physiological abnormality (Id.). Women, low income populations, and the elderly are more likely to suffer from the condition (Id.). Constipation has been reported to lead to lower quality of life and other difficulties (see Wald et al. (2007) *Aliment Pharmacol Ther.* 26:227-36).

The symptoms associated with CIC can be resistant to treatment (see Johanson and Kralstein (2007) Aliment Pharmacol Ther. 25:599-608). One treatment is an increase in dietary fiber and increased hydration (see Suares and Ford (2011) *Aliment Pharmacol Ther.* 33(8):895-901). Other treatments include laxatives, both osmotic and stimulant, $5\text{-HT}_4$ antagonists, prosecretory agents, bile acid transporter inhibitors, probiotics, and biofeedback (see Ford et al. (2014) *Am J Gastroenterol.* 109:S2-S26). These approaches to the treatment of CIC are limited and for some subjects there are significant drawbacks that have not been resolved. It would be desirable to provide a source of relief for constipation that would permit dosing adjustments to optimize efficacy and safety and that would be pleasant to consume to improve subject compliance. The treatment should not have the safety issues associated with oral phosphate laxatives, have an acceptable safety profile, and be effective in numerous types of constipation.

One such treatment, lactitol, is utilized in patients. Lactitol function depends on retention of the drug in the intestine of the patient. It is suspected that some lactitol is absorbed into the blood of subjects after administration. This absorption can lead to reduced efficacy and potential other side effects. Therefore, there is a need to find an improved administration of lactitol in subjects for effective treatment of CIC treatment.

SUMMARY

Disclosed herein are methods and compositions (alternatively, "formulations") for the safe and effective treatment of CIC. The methods allow for administration of formulations comprising lactitol such that the formulations treat CIC while also diminishing the amount and variability of absorption of lactitol into the serum of the subject. The disclosed methods and formulations therefore improve the safety profile of the drug, reduce variability in the amount of the dose that is retained in the colon, and improve the drug's efficacy by keeping the lactitol in the intestines of the subject.

In addition, the disclosed methods relate to the taking of lactitol during or after a meal is consumed by the subject. The fed subjects show a decreased absorption of lactitol into the plasma and a decrease in the inter-subject variability. The methods disclosed herein further reduce the AUC of lactitol such that additional lactitol remains in the intestines to improve the efficacy of lactitol.

Aspects of the methods disclosed herein include a method of reducing plasma concentrations of lactitol in a subject. The method comprises administering an effective amount of a formulation comprising lactitol after the subject begins consuming a meal. As used herein, the term "a" means one or more unless specifically defined otherwise.

In certain embodiments, the meal is a high calorie meal. In other embodiments, the high calorie meal comprises at least about 500 calories. In still other embodiments, the high calorie meal comprises 50% fat calories.

In further embodiments, the formulation is administered as a powder. In more embodiments, the formulation is administered as the powder reconstituted in a solution.

In other embodiments, the effective amount of lactitol comprises from about 5.0 grams to about 30 grams. In still other embodiments, the effective amount of lactitol comprises from about 10.0 grams to about 25 grams. In yet other embodiments, the effective amount of lactitol comprises about 21.0 grams.

In some embodiments, the effective amount is divided into two or more doses. In other embodiments, the effective amount is divided into two doses. In still other embodiments, the solution is selected from the group consisting of juice, soda, water, and balanced electrolyte solution. In more embodiments, the formulation is a liquid. In yet further embodiments, the formulation comprises one or more of natural flavoring, artificial flavoring, or preservatives.

In certain embodiments, the method further comprises administering an agent selected from the group consisting of polyethylene glycol, sulfate salts, magnesium salts, stimulant laxatives, and lubiprostone. In particular embodiments, the agent is lubiprostone.

In certain embodiments, the subject has three or more spontaneous bowel movements. In particular embodiments, the spontaneous bowel movements occur within a seven day period. In more particular embodiments, the formulation is provided in bulk.

In some embodiments, the AUC in a fed subject is at least 2 times smaller than the AUC in a fasted subject. In some other embodiments, the subject has plasma concentrations of lactitol of less than 1000 ng/mL four hours after administration of the effective amount of lactitol.

In some embodiments, the effective amount of lactitol is administered at least 30 minutes after the subject begins consuming the meal. In more embodiments, the effective amount of lactitol is administered at least 45 minutes after the subject begins consuming the meal. In further embodiments, the effective amount of lactitol is administered at least 1 hour after the subject begins consuming the meal. In still further embodiments, the effective amount of lactitol is administered after the subject has consumed the meal.

Aspects of the formulations disclosed herein comprise an effective amount of lactitol. In certain embodiments, the effective amount is administered to a total dosage that is sufficient to induce spontaneous bowel movements in a subject. In particular embodiments, the total dosage is from about 5.0 grams to about 30.0 grams. In other embodiments, the total dosage is from about 10.0 grams to about 25.0 grams. In still other embodiments, the total dosage is about 10.5 grams to about 21.0 grams. In particular embodiments, the formulations can further be administered in one or more doses to attain the total dosage. In more particular embodiments, the formulation is administered to 21.0 grams can be administered in two doses of 10.5 grams. In further embodiments, the total dosage can be administered in two or more doses separated by at least two hours, at least three hours, at least four hours, at least five hours, at least six hours, or at least 12 hours.

BRIEF DESCRIPTION OF THE FIGURES

The present exemplary non-limiting implementation will be described in detail herein with reference to the following drawings, in which like reference numerals refer to like elements, and wherein:

FIG. 1 is a chart showing the plasma concentrations of lactitol in subjects who were in a fed state (○) and subjects who were in a fasted state (●).

DETAILED DESCRIPTION

1. Lactitol Formulations

Disclosed herein are formulations comprising lactitol. Lactitol is an osmotic laxative. Specifically, lactitol is a poorly absorbed, colonically metabolized sugar alcohol. Previous studies have shown that lactitol provides relief from the symptoms of CIC through the rapid induction of subject-controlled bowel movements. While lactitol appears to be minimally absorbed in the small intestine, colonic microbes split lactitol into D-galactose and D-sorbitol, which are fermentable to organic acids including lactic, formic, propionic, butyric and acetic acids (Patil et al. (1987) *Br J Nutr.* 57(2):195-9). The osmotic properties of the small organic molecules consistently point to their pharmacodynamic effects as dependent on water retention with the stool. Lactitol is generally considered to be pharmacologically inert and is often referred to as a "prebiotic" with no specific receptor targets for its laxative action.

Lactitol is a simple monosaccharide sugar alcohol, a synthetic derivative of the milk sugar lactose that was discovered in the 1920s. It is a dry, free flowing powder, readily soluble in aqueous solutions. As shown by the structure diagrams below, it is an analog of the disaccharide lactulose.

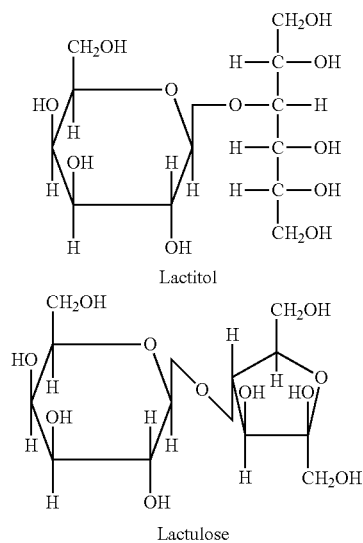

Lactitol

Lactulose

Lactitol is not degraded by the galactosidase enzymes of the small intestine. However, colonic microflora degrade lactitol extensively in rats so that lactitol elevated the proportions of acetic acid and lowered proportions of butyric acid in the hindgut of rats. The osmotic effects of these organic acids appear to provide the pharmacodynamic basis for lactitol's laxative action. Increased output of moist feces was seen in all animals species studied in a dose-related manner. The highest doses tested caused frank diarrhea in some studies. In some studies, total serum cholesterol and triglycerides were reduced equally in rats fed diets containing 7% sorbitol or lactitol. By acidifying fecal contents, lactitol lowered ammonia levels in animal models of hepatic encephalopathy, perhaps as a result of production of the poorly absorbed ammonium ion that follows lowering the cecal pH. Rats fed a diet containing 5% of lactitol for two weeks displayed a significant increase of calcium absorption.

Because lactitol is extensively degraded to organic acids in the colon, there are no published studies on its level in blood after administration due to the belief that lactitol is not absorbed into the serum (see, e.g., Metzger et al. (1988) *Eur J Clin Pharmacol.* 35(1):97-9). Some have estimated that only 0.6% of an oral dose of lactitol is excreted in urine. Similar to what is found in animals, lactitol is extensively metabolized in the human colon, making available a significant proportion of the metabolites for colonic absorption. Unlike in animals, lactitol does not seem to stimulate calcium absorption in humans, although in one study when 15 grams of lactitol was administered along with calcium in solution to fasting volunteers, calcium absorption was diminished. Administering lactitol increases fecal Bifidobacteria levels, while other bacteria (fecal anaerobes, aerobes, Enterobacteriaceae or lactobacilli) were unaffected. After the ingestion of 25 grams lactitol, xylitol, or glucose by eight healthy male volunteers the rise in plasma glucose was significantly greater 30 and 60 minutes after ingestion of glucose while no rise in plasma glucose followed ingestion of lactitol.

Due to the actions of lactitol in the intestines, it is optimal that the amount of lactitol uptake in the blood of a subject be reduced and its variability minimized. In addition, reducing lactitol absorption would improve the efficacy of treatment and reduce potential side effects.

The disclosed formulations comprise lactitol and can be administered in such a way to reduce the absorption of lactitol in the plasma. In particular embodiments, the disclosed formulations comprise lactitol monohydrate, NF. The disclosed formulations, when administered with food, reduce the absorption of lactitol and improve the pharmacokinetic profile of the formulations. The disclosed formulations can be administered at least about 30 minutes after a meal, at least about 45 minutes after a meal, or at least about 1 hour after a meal.

Lactitol can be administered as a solid oral dosage form. Examples of solid oral dosage forms include powder, tablet, capsule, compressed capsule, gel capsule, or caplet. In particular embodiments, the solid oral dosage form is a powder. Each solid oral dosage form can be administered such that a subject receives a dose of from about 0.01 grams/kg body weight to about 5.0 grams/kg body weight. In particular embodiments, the solid oral dosage form is administered such that a subject receives a dose of from about 0.1 grams/kg body weight to about 1.0 grams/kg body weight.

In some embodiments, the formulations are administered to a total dosage of from about 5.0 grams to about 30.0 grams. In other embodiments, the formulations are administered to a total dosage of from about 10.0 grams to about 25.0 grams. In still other embodiments, the formulations are administered to a total dosage of about 10.5 grams to about 21.0 grams. The formulations can further be administered in one or more doses to attain the total dosage. For instance, a formulation administered to 21.0 grams can be administered in two doses of 10.5 grams. In further embodiments, the total dosage can be administered in two or more doses separated by at least two hours, at least three hours, at least four hours, at least five hours, at least six hours, or at least 12 hours.

The disclosed formulations can be administered as a powder. It should be noted that the powder can be provided to subjects in packets or bottles in pre-measured amounts or provided in bulk with instructions to measure out the proper dosage. In some embodiments, lactitol can be added to the food in a meal or dissolved in a liquid. For instance, the lactitol formulation can be mixed with food. When administered as a liquid, the formulation can be consumed by reconstituting a powder into a sufficient volume of liquid to dissolve the lactitol. Examples of liquids include water, fruit juices, electrolyte solutions, or aqueous solutions comprising natural or artificial flavorings. Exemplary volumes of liquid include from about 50 mL to about 1 L, from about 100 mL to about 500 mL, from about 200 mL to about 400 mL. In other embodiments, the powder formulation is dissolved in 50 mL to 300 mL of water. It should be noted that the volume of water can be adjusted so long as the laxative effective of the powder formulation is not adversely affected.

In certain embodiments, the solid oral dosage form can be in the form of a tablet, capsule, compressed capsule, gel capsule, or caplet. In such embodiments, the solid oral dosage forms can further comprise one or more excipients. The one or more excipients (e.g., soluble) are selected from the group consisting of binders, lubricants, glidants, disintegrants, and combinations thereof. Exemplary excipients include binders such as copolyvidone, gelatin, hydroxypropyl cellulose, hydroxypropyl methylcellulose, hypromellose, lactose anhydrous, povidone, and polyethylene oxide. Other exemplary excipients include emulsifying agents such as hydroxypropyl cellulose, polaxamer 407, and sodium lauryl sulfate. The formulations can comprise lubricants such as polyethylene glycol, polaxamer 407, sodium lauryl sulfate, sodium benzoate, sodium dodecyl sulfate, sodium caprylate, and sodium stearyl sulfate, magnesium stearate, stearic acid, hydrogenated vegetable oil, and glyceryl palmitostearate. Further exemplary excipients include disintegrants such as citric acid, croscarmellose sodium, and povidone.

The solid oral dosage forms can be tableted using standard production style equipment and techniques (Bogda, Michael J. Ch. 260, "Tablet Compression: Machine Theory, Design, and Process Troubleshooting" in *Encyclopedia of Pharmaceutical Technology, Third Edition*, 2006). In other embodiments, the pharmaceutical tablet formulation is encapsulated.

Certain embodiments of the disclosed solid oral dosage forms further comprise a coating. For instance, the coating can be an enteric coating. Polymers useful for enteric coatings polymethacrylates such as methacrylic acid/ethyl acrylate, cellulose esters such as cellulose acetate phthalate (CAP), cellulose acetate trimellitate (CAT), hydroxypropylmethylcellulose acetate succinate (HPMCAS), and polyvinyl derivatives such as polyvinyl acetate phthalate (PVAP). In other embodiments, the coatings comprise hydroxypropylmethyl cellulose, methylcellulose, hydroxypropylcellulose, carboxymethylcellulose sodium, polyethylene glycols, synthetic polymers, shellac, corn protein zein, polysaccharides, polyvinyl alcohol, polyethylene glycol, Kollicoat IR (polyvinyl alcohol-polyethylene glycol co-polymer), Kollicoat SR 30D (Polyvinyl acetate stabilized with polyvinylpyrrolidone and sodium lauryl sulfate), or gelatin. Methods of making enteric coatings are well known in the art and include film formation and aqueous dispersion techniques (Porter S, Verseput R, Cunningham C. (1997) *Pharm. Technol.* 21: 60-70; Twitchell A, Hogan J, Aulton M. (1995a) *S.T.P. Pharm. Sci.* 5: 190-195; Twitchell A, Hogan J, Aulton M. (1995b) *Drug Dev Ind Pharm* 21:1611-1619; Tobiska S, Kleinbudde P. (2003) *Pharm. Dev. Tech.* 8: 39-46; Poukavoos N, Peck G. (1994) *Drug Dev. Ind. Pharm.* 20: 1535-1554; Wilson K, Crossman E. (1997) *Drug Dev Ind Pharm* 23:1239-1243).

Aspects of the solid oral dosage forms disintegrate rapidly in aqueous solutions such as gastrointestinal fluids. In some embodiments, the solid oral dosage forms disintegrate in less than 30 minutes. In particular embodiments, the solid oral dosage forms disintegrate in less than about 15 minutes. The disintegration time for such tablet compositions avoid ulcer complications. Such advantages are accomplished by using a minimal amount of water-soluble excipients.

Certain solid oral dosage forms have the characteristic that at least 80% of the tablet formulation dissolves within 30 minutes using Apparatus 2. In certain embodiments, at least 75% of the tablet dissolves within 30 minutes using Apparatus 2. In other embodiments, at least 85% of the tablet formulation dissolves within 30 minutes using Apparatus 2. In particular embodiments, at least 90% of the tablet formulation dissolves within 30 minutes using Apparatus 2. In still more particular embodiments, at least 95% of the tablet formulation dissolves within 30 minutes using Apparatus 2. In other embodiments, at least 98% of the tablet formulation dissolves within 30 minutes using Apparatus 2. In some embodiments, at least 100% of the tablet formulation dissolves within 30 minutes using Apparatus 2.

The determination of tablet disintegration is accomplished using in vitro test methods provided in the United States Pharmacopoeia (see e.g., United States Pharmacopoeia, Vol. 36 <711> Dissolution, pages 307-313, applying Apparatus 2 (Paddle Apparatus)). Briefly, a paddle is formed from a blade and a shaft and is used as the stirring element driven by a motor at a specified speed (e.g., 50 rpm). The tablet is placed into an inert (typically glass) transparent vessel containing about 900 mL of the dissolving media (oftentimes water). The dissolution media in the vessel is maintained at 37° C. using a water bath, or other suitable means, to simulate human body temperature. The paddle is rotated in a uniform manner (minimal wobble) at a specified height above the bottom of the vessel, providing turbulence in the vessel similar to that of the human digestive tract. As the tablet dissolves, and after a specified period of time (e.g., 15 minutes, 30 minutes, or up to an hour), a sample of the dissolution media with the dissolved tablet is removed and tested for active ingredients. The test results may be set at, for example, Not Less Than (NLT) 80% (Q) in 15 minutes. The (Q), according to USP (refer to USP method <711> Interpretation for Immediate Release Dosage form, page 312), means that after testing 6 tablets (termed S1), the results of all 6 tablets are greater than Q+5, or 85%. If any tablets do not meet the criteria, another 6 tablets are tested (termed S2), and the average of the 12 tablets is equal to or greater than Q (80%), and no individual tablet result is less than Q-15 (65%). If any of the 12 tablets do not meet the criteria, another 12 tablets are tested (termed S3), and the average of the 24 tablets is equal to or greater than Q (80%), no more than 2 individual tablet results are less than Q-15 (65%), and no individual tablet result is less than Q-25 (55%). In particular embodiments, a dissolution media other than water (e.g. gastric fluid, buffered solution, etc.) is used. In particular embodiments, the paddle speed is adjusted to 75 rpm or higher. In still other embodiments, the sampling time is from about 30 minutes, about 45 minutes, or at least 60 minutes. In more embodiments, the Q is NLT 75% (Q), NLT 85% (Q), or any Q that is acceptable. In still other embodiments, a basket assembly is used.

In other aspects, the tablets are tested for physical disintegration by applying the USP Disintegration test (see USP Vol. 36 Physical Tests, method <701> Disintegration, pages 305-306 for plain coated or uncoated tablets). Six tablets are placed into separate tubes of a basket rack assembly of specified size and shape. The assembly is immersed in an alternating up and down motion into a beaker filled with disintegration media (e.g., water) maintained at 37° C. The apparatus may or may not have specialized disks for each tube. After a specified time period, the operator visually evaluates the apparatus for complete disintegration, defined as that state in which any residue of the unit (any of the 6 tablets), except fragments of insoluble coating or capsule shell, remaining on the screen of the test apparatus or adhering to the lower surface of the disk, if used, is a soft mass having no palpably firm core.

Additional aspects of the disclosed formulations comprise a liquid. For instance, lactitol can be dissolved in an aqueous solution and provided to subjects in pre-measured volumes or in bulk solution for with instructions on measuring out the proper doses. In certain embodiments, the lactitol solution is provided as a concentrate to be diluted prior to administration. The liquid formulation disclosed herein can be made using standard procedures in the art (see Remington: The Science and Practice of Pharmacy, Troy and Beringer, eds., 21$^{st}$ Edition, Lippincott Williams & Wilkins: Baltimore 2006).

The formulations disclosed herein can comprise one or more excipients for improving shelf life or flavor. The formulations for example can include one or more preservatives. Examples of preservatives include acetic acid, ascorbic acid, calcium ascorbate, erythorbic acid, isoascorbic acid, sodium ascorbate, sodium erthorbate, sodium isoascorbate, benzoic acid, Ethyl lauroyl arginate, methyl-p-hydroxy benzoate, methyl paraben, and calcium sorbate. The formulations can also comprise one or more artificial or natural flavorings. Examples of artificial or natural flavorings include isoamyl acetate, ethyl propionate, methyl anthranilate, limonene, ethyl decadienoate, allyl hexanoate, natural fruit extract, natural fruit flavorings, natural extracts, oils, or other flavorings known to those of ordinary skill in the art.

It should be noted that the formulations disclosed herein can be deviated from regarding the amounts of potential excipients, flavoring agents, preservatives, or other inactive ingredients.

2. Methods of Treating CIC

Disclosed herein are methods of administering the laxative formulations comprising lactitol to reduce the serum plasma concentrations of lactitol during treatment, thereby improving the efficacy of the formulation. Aspects of the disclosed methods comprise administering to a subject an effective amount of the formulation to induce or cause the subject to have spontaneous bowel movements during the treatment period. The term "effective amount" refers to the amount of formulation that produces one or more spontaneous bowel movements. The effect of the activity of the disclosed formulations is to treat CIC. As disclosed above, an effective amount of lactitol when administered to a subject will induce bowel movements. However, it has been discovered that administering lactitol to subjects who consume a meal reduces the absorption of lactitol into the blood of the subject.

It should be noted that the disclosed methods comprise the formulations producing a laxative effect in the subject such that the subject has a spontaneous bowel movement. In certain embodiments, the formulation produces a laxative effect such that the subject has at least three spontaneous bowel movements in a seven day treatment period when the disclosed formulations are taken either daily or as needed by the subject. In some embodiments, the subject is administered solid oral dosage forms to induce a laxation event. In particular embodiments, solid oral dosage form is a powder. The solid oral dosage forms are administered to a total dosage of from about 5.0 grams to about 30.0 grams. In other embodiments, the formulations are administered to a total dosage of from about 10.0 grams to about 25.0 grams. In still other embodiments, the solid oral dosage forms are administered to a total dosage of about 10.5 grams to about 21.0 grams. The solid oral dosage forms can further be administered in one or more doses to attain the total dosage. For instance, a solid oral dosage form administered to 21.0 grams can be administered in two doses of 10.5 grams. In further embodiments, the total dosage can be administered in two or more doses separated by at least two hours, at least three hours, at least four hours, at least five hours, at least six hours, or at least 12 hours.

Aspects of the methods comprise administering an effective amount of lactitol to a subject within about 30 minutes of starting a meal. In some embodiments, the formulations are administered at least about 30 minutes after consuming a meal. In other embodiments, the formulations are administered at least about 45 minutes after consuming a meal, at least about 1 hour after consuming a meal, or at least about 1 hour after consuming a meal. In particular embodiments, the formulations are administered at least about 45 minutes after beginning consumption of a meal, at least about 1 hour after beginning consumption of a meal, at least about 1 hour after beginning consumption of a meal, or at least about 2 hours after beginning consumption of a meal. In certain embodiments, the effective amount of lactitol can be co-administered either simultaneously or consecutively with another agent such as an osmotic agent or a stimulant laxative. Examples of agents that can be co-administered with lactitol are agents that also can aid in the treatment of constipation. Such agents include polyethylene glycol, sulfate salts, magnesium salts, stimulant laxatives, and/or lubiprostone. In some embodiments, the agent is lubiprostone. The doses of such agents can be adjusted according to the needs of the subject being co-administered the agents.

In certain embodiments, the meal has a calorie content of at least 500 calories. In other embodiments, the calorie content is at least 800 calories. In still other embodiments, the calorie content is about 1000 calories. The calorie content of the meal can also be as high as 1500 calories. The meal can further be a high fat meal. A high fat meal is a meal in which about 40%, 50%, 60%, or 70% of the calories are from fat content. In particular embodiments, a high fat meal is a meal in which about 50% of the calories are from fat content of the meal.

The methods disclosed herein can reduce the area under the curve ("AUC") of plasma lactitol concentrations significantly when a subject is in the fed state as compared to the fasted state (e.g., having taken the formulation without eating a meal within 2 hours). The disclosed methods can show a reduction of AUC in the fed state as compared to the fasted state of at least about 20%. In certain embodiments, the AUC is reduced in the fed state by at least about 50%, 100%, 200%, 300%, 400%, 500%, 600%, 700%, 800%, or at least about 900%. AUC in the fed state can be reduced by up to about 1000%.

Subjects in the fed state can have plasma lactitol concentrations from about 300 ng/ml plasma to about 900 ng/ml plasma from about 1 hour to about 8 hours post-dosing. As compared to the fasted state, the fed state can show a reduced plasma lactitol concentration for up to 15 hours post-dosing. For instance, subjects administered an effective amount of lactitol can exhibit reduced plasma lactitol concentrations 10 hours post-dose as compared to subjects administered lactitol in the fasted state 10 hours post-dose.

Some aspects of the methods disclosed herein involve administering the formulations as a powder or liquid. When administered as a powder, the subject can dissolve the powder in a volume of aqueous solution. In some embodiments, the powder is dissolved in water. The objective is to allow the powder formulation to be administered in a palatable form for the subject, while also allowing the laxative effect of the salts to relieve the constipation of the subject. In some embodiments, the subject dissolves the powder in 50 mL to 100 mL of aqueous solution. However, the subject can dissolve the powder in volumes of aqueous solution from 30 mL to 200 mL, depending on the amount of powder to be consumed.

When administered as a liquid, the formulation can include flavorings to improve the palatability of the liquid. Examples of artificial or natural flavorings include, but are not limited to, lemon, lime, grape, cherry, and orange. Furthermore, the liquid formulation can be divided into doses to be taken by the subject.

In particular embodiments, the formulation is administered at least once per day. In more particular embodiments, the formulation is administered on an as needed basis by the subject.

Additionally, the disclosed formulations can be administered with a sufficient quantity of liquid to ease swallowing of the solid oral dosage forms or to avoid dehydration. In particular embodiments, the total volume of liquid administered to the subject is from about 50 ml to about 500 ml. In some embodiments, the subject consumes any volume of liquid deemed necessary by a medical professional.

One of ordinary skill in the art will recognize a range of variations and equivalents based on this disclosure of formulations and methods. Such variations and equivalents are intended to fall within the scope of this disclosure. One of ordinary skill in the art will also recognize that the disclosed embodiments are illustrative and that equivalents of such embodiments also fall within the scope of this disclosure.

EXAMPLES

Example 1. Treatment of CIC with Lactitol Formulations

The study was a randomized, double-blind, parallel group, multi-center study in constipated adult subjects.

Approximately 400 constipated, but otherwise healthy patients were randomized into the study. A "completed" subject was defined as one who took the study treatment and completed 12 weeks of treatment.

Subjects were provided packets containing 10.5 grams of the disclosed formulation. Subjects were instructed to mix the contents of two (2) packets (approximately 21 g) with 4-8 ounces of juice or other beverage and take once daily. Subjects that developed persistent diarrhea or loose stools were allowed to adjust their dose down to 10.5 g (1 packet) per day.

Lubiprostone (Amitiza) was provided in polyethylene bottles containing over encapsulated Amitiza capsules to maintain the treatment blind. Subjects were instructed to take the capsules twice daily (AM and PM) with food and water.

In the event that subjects required additional constipation support, subjects were dispensed bisacodyl tablets at each study visit. Subjects were instructed to take 5-10 mg of bisacodyl if they were experiencing severe discomfort due to their constipation, or had not had a BM in 4 days. No more than 6 tablets (30 mg) of bisacodyl should be taken in a week. If a subject did not have a bowel movement within 24 hours of taking a bisacodyl dose, a second dose was taken. If after the second bisacodyl dose the subject did not have a BM within 24 hours, the subject contacted the site. The investigator then considered having the subject return for an evaluation and/or discontinuing the subject from the study Study Procedures Study procedures are described as follows. Acceptable deviations from the visit schedule are indicated. These variations were not cumulative; i.e. visits should always be scheduled in relationship to Visit 2 (Day 0).

At the screening visit, the following procedures were undertaken:

Subject was fully informed about the study and gave written agreement to study participation in the form of a signed informed consent form and assigned a subject number Assessed eligibility (refer to inclusion/exclusion criteria)

Reviewed of medications

Medical history including history of constipation (ROME criteria)

Physical examination (including height and bodyweight)

Vital signs: including assessment of orthostatic hypotension (while seated and after standing for a minimum of 2 minutes) and temperature A 12-lead ECG was performed by qualified, trained site personnel. ECG output was reviewed by a physician investigator. Any clinically significant cardiac abnormalities identified on the ECG disqualified a subject. Data from the ECG was collected in the eCRF.

Urine pregnancy test (if applicable)

Provided the subject an electronic diary and reviewed instructions with the subject in detail to ensure full understanding (refer to Section 4.1.3).

Dispensed rescue bisacodyl. Subjects were allowed to take 5-10 mg of bisacodyl if they were experiencing severe discomfort due to their constipation, or had not had a BM in 4 days.

Instructed subject to maintain their normal dietary habits during study participation.

Scheduled the next study visit to occur after 14 full screening days.

Subjects that were ineligible due to prohibited medication use washed out for a period of 14 days (72 hour washout only for laxatives). No additional procedures were performed on these patients until after they had completed washout. Subjects received a reminder card detailing the washout period. Rescue bisacodyl was not dispensed at this visit. When subjects returned following washout, concomitant medications were reviewed, physical exam, vital signs, and urine pregnancy test were performed (if not done previously).

Subjects were enrolled into the study only when they had given their written, informed consent to participate.

Subjects were asked to use an electronic subject diary to self-report their bowel movement and medication experiences each day. Subjects were required to enter data on each bowel movement as soon as possible following completion. Each dosing episode of study medication were entered. Investigators were sent a summary of all data for each subject entered into the electronic diary for the week.

Subjects were required to report each bowel movement which occurred during the Screening Period. At the end of each screening day, subjects were prompted to enter any missed bowel movements or rescue medication into the electronic diary.

Subjects returned to the study center as soon as possible after the 14 day Screening Period for Visit 2.

BM Entry Criteria— to be eligible for randomization, subjects met the following criteria related to their Screening Period BMs:
- average of fewer than 3 complete spontaneous bowel movements (CSBMs) per week during the 14 day Screening Period. A CSBM was defined as a bowel movement which has occurred with no rescue laxative use in the prior 24 hours and is accompanied by a sense of complete evacuation
- average of fewer than 6 spontaneous bowel movements (SBMs) per week during the 14 day Screening Period. An SBM was defined as a bowel movement which has occurred with no rescue laxative use in the prior 24 hours
- No more than 1 SBM with a Bristol Stool rating of 6
- No SBMs with a Bristol Stool rating of 7.

Diary Compliance Criterion— to be eligible for randomization, a subject must have completed an average of 5 bowel movement diary entries per week or more during the 14 day Screening Period.

Subjects that meet the BM and Diary Compliance Criteria were randomized. Treatment assignments were based on a randomization schedule implemented by Braintree Laboratories prior to distribution of study medication to the site. Following receipt of a sequential series of study medication kits, site personnel were dispensed the lowest numbered kit available in order to maintain the randomization schedule. Dispensing kits out of order was considered a protocol violation.

A subject with clinically significant electrolyte abnormalities, determined by the expertise of the clinician and deemed as a potential safety issue by the clinician, was discontinued at the clinician's discretion. If the subject was withdrawn, they discontinued study treatment immediately and returned to the clinic for an end of study visit as soon as possible.

Vital signs were taken. A 12-lead ECG were performed by qualified, trained site personnel. ECG output was reviewed by a physician investigator (or central physician reader designated by the Sponsor). Any clinically significant cardiac abnormalities identified on the ECG disqualified a subject. Data from the ECG were collected in the eCRF. Subjects were queried for any adverse events or changes to their concomitant medications.

Subjects continued to report their bowel movement experiences each day during the Treatment Period. In addition, during the Treatment Period, subjects reported each study and rescue medication dosing event, noting the time and dose.

During Visit 2, subjects were provided with instructions on how to take the study medication and rescue medication. A 30 day supply of study drug was dispensed per subject to include sixty (60) packets of powder, one bottle of capsules and one packet of rescue medication. Subjects took a daily dose of 2 packets of study powder and 2 capsules until they returned for Visit 3. Subjects were instructed to return all medication (including bisacodyl) and components at Visit 3.

Treatment Period

Starting on Treatment Day 1 (the morning after randomization), subjects measured out two (2) packets of study powder and ingested it mixed in a beverage of their choice followed by 1 study capsule orally with food and water in the morning. Subjects took a second capsule in the afternoon/evening with food and water. When possible, subjects took each dose at approximately the same time every day. Subjects that developed persistent diarrhea or loose stools contacted their study center. Dose adjustments due to persistent diarrhea were allowed. Any subject requiring a dose adjustment decreased both dose forms concurrently by taking one (1) packet of powder daily and one capsule daily (AM dose). No other decreased dose regimens was allowed.

Following the first dose of study medication (and all subsequent doses), subjects reported the time and number of packets and capsules taken in the electronic diary. All bowel movements occurring after the Day 1 study medication dose were reported in the electronic diary in real time.

Subjects returned to the clinic for Visit 3 (Day 28+/−2 days) and Visit 4 (Day 56+/−2 days). Vital signs were taken. A 12-lead ECG were performed by qualified, trained site personnel. ECG output was reviewed by a physician investigator. Investigators discontinued subjects with clinically significant ECG abnormalities. Data from the ECG was collected in the eCRF. Study personnel reviewed returned full packets, bottle of capsules and rescue bisacodyl for accountability purposes and for consistency with the electronic diary reporting. Study personnel discussed any electronic diary reporting irregularities (e.g. excessive study medication or rescue bisacodyl use, reporting compliance). Subjects were queried for any adverse events or changes to their concomitant medications. Samples for chemistry, hematology and urinalysis were repeated.

Subjects suspected by the investigator of having developed lactic acidosis, characterized by abnormally low bicarbonate with high anion gap (also outside the normal range), returned for a redraw to test for lactate. Subjects with high lactate levels believed to be caused by the study medication were discontinued.

A 30 day supply of study medication (60 packets of powder and 1 bottle of capsules) along with 1 packet of rescue bisacodyl was dispensed at each visit. Unused product was not redispensed. No rescue medication was redispensed. Subjects were instructed to bring all medication (including bisacodyl) and components at each follow up visit.

Subjects returned at after a full 84 days of dosing (+4 days) for their final clinic visit. Vital signs will be taken. A 12-lead ECG were performed by qualified, trained site personnel. ECG output reviewed by a physician investigator. Data from the ECG were collected in the eCRF. A physical examination were performed (including bodyweight). Study personnel reviewed returned full packets, bottle of capsules and rescue bisacodyl for accountability purposes and for consistency with the electronic diary reporting. Study personnel discussed any electronic diary reporting irregularities (e.g. excessive study medication or rescue bisacodyl use, reporting compliance). Subjects were queried for any adverse events or changes to their concomitant medications. Samples for chemistry, hematology and urinalysis were repeated as outlined in Section 4.2.1. Subjects suspected by the Investigator of having developed lactic acidosis (as described in Section 4.3.2) returned for a redraw to test for lactate.

At Day 98, approximately 2 weeks after the last study visit or early term visit, site personnel contacted subjects by telephone to query if any new adverse events had occurred and if any adverse events ongoing at Visit 5 had resolved.

The use of concomitant medication were recorded from 7 days prior to Visit 1 until the end of the study at the telephone contact on Day 98. Subjects enrolled in this study were not permitted to take any laxatives (other than the sponsor supplied rescue bisacodyl), whether prescription or over-the-counter, from Visit 1 until after completion of Treatment Day 84. Any restricted laxative use during the study may have resulted in termination of subject's participation. Subjects were not allowed to initiate treatment with any constipating medication.

Adverse Events

An Adverse Event (AE) is any untoward medical occurrence associated with the use of a drug in humans, whether or not considered drug related. An AE can therefore be any unfavorable and unintended sign (including a clinically significant abnormal laboratory finding), symptom, or disease temporally associated with the use of a medicinal (investigational) product.

Adverse event collection coincided with the patient providing informed consent to participate in the study and concluded with the end of study participation at Day 98 (2 week follow-up phone call). Patients with clinically significant laboratory results at Visit 5 which were classified by the Investigator as adverse events returned for a repeat blood draw. Patients were instructed to report promptly adverse events to the Investigator. The Investigator recorded the date/time of report, date/time of onset, description of the adverse event, severity of adverse event, action(s) taken regarding treatment of the event, action(s) taken regarding study participation, duration of adverse event, and the Investigator's assessment of relationship of adverse event to study treatment.

The Investigator assessed the severity of each adverse event using the following categories:

| Grade | Severity | Description |
|---|---|---|
| 1 | Mild | Barely noticeable, does not influence functioning |
|   |   | Causing no limitations of usual activities |
| 2 | Moderate | Makes participant uncomfortable, influences functioning |
|   |   | Causing some limitations of usual activities |
| 3 | Severe | Severe discomfort, treatment needed |
|   |   | Severe and undesirable, causing inability to carry out usual activities |
| 4 | Life threatening | Immediate risk of death |
|   |   | Life threatening or disabling |
| 5 | Fatal | Causes death of the participant |

The Investigator assessed the relationship to study drug for each adverse event using the following categories:

| Categories of Attribution: | Description |
|---|---|
| UNRELATED | There is no evidence of any causal relationship. |
| POSSIBLE | There is some evidence to suggest a causal relationship (e.g., the event occurred within a reasonable time after administration of the trial medication). However, the influence of other factors may have contributed to the event (e.g., the subject's clinical condition, other concomitant events). |
| PROBABLE | There is evidence to suggest a causal relationship, and the influence of other factors is unlikely. |
| DEFINITE | There is clear evidence to suggest a causal relationship, and other possible contributing factors can be ruled out. |

In Phase 3 studies, adverse events associated with Lactitol administered at doses required for effective treatment of constipation included flatulence, nausea, vomiting, abdominal cramping or pain and bloating. These adverse reactions were transient and subsided rapidly upon dose adjustment or cessation.

Lubiprostone is contraindicated in patients with known or suspected mechanical gastrointestinal obstruction. Most common adverse reactions (incidence >4%) in chronic idiopathic constipation are nausea, diarrhea, headache, abdominal pain, abdominal distention and flatulence.

Serious Adverse Reactions and Discontinuation of Study

A Serious Adverse Event (SAE) is any untoward medical occurrence that results in at least one of the following outcomes: Results in death; Is life-threatening; Requires in subject hospitalization or prolongation of existing hospitalization; A persistent or significant incapacity or substantial disruption of the ability to conduct normal life functions; Is a congenital anomaly/birth defect; and Requires medical or surgical intervention to prevent permanent impairment or damage.

SAE collection coincided with the subject providing informed consent to participate in the study and concluded 30 days after date of last study medication dose. If a serious and/or unexpected adverse event occur, the Investigator notified Braintree Laboratories immediately. The Investigator made a decision regarding continuing study participation, and may request input from Braintree Laboratories. The Investigator was responsible for recommending or providing the subject with appropriate medical therapy. All subjects experiencing serious adverse events were followed until satisfactory resolution occurred. Braintree Laboratories was kept apprised of all follow-ups relative to serious adverse events. In addition, Investigators complied with the SAE reporting requirements of the Institutional Review Board with oversight of the study.

Data Analysis

Sample Size:

Four hundred subjects will be randomly assigned to the formulation (21 g/day dose) or lubiprostone in a ratio of 1:1 (200 the formulation: 200 lubiprostone). The definition of a weekly responder is based on weekly assessments of complete spontaneous bowel movements (CSBMs).

Null and Alternative Hypothesis:

The primary objective of this study was to compare the safety and efficacy the formulation to lubiprostone in patients with constipation. To establish this, the primary comparison of interest was on the overall responder percentage based on 12 weeks of treatment. A weekly responder was a subject who had an average of ≥3 CSBMs/week and an average increase from baseline of >1 CSBM/week in that week.

Baseline comparability of the following demographic and baseline characteristics for the treatment groups were performed.

Age
Gender
Race/ethnicity
Constipation History
Efficacy Analyses:

The primary efficacy endpoint was assessed on the basis of a binary outcome of overall treatment success or failure. The primary efficacy endpoint was proportion of subjects who were weekly responders for 9 out of the 12 weeks of treatment, with at least 3 of these weeks occurring in the last 4 weeks of treatment. A weekly responder was a subject who had an average of ≥3 CSBMs/week and an average increase from baseline of >1 CSBM/week in that week. A CSBM was a bowel movement that occurs with no rescue laxative use in the previous 24 hours and that was accompanied by a sense of complete evacuation. The following equation will be used to calculate the weekly CSBM frequency: CSBM frequency=7×(Number of CSBMs/number of days with non-missing CSBM assessments).

If a subject had fewer than four days of data observed for a week, then that subject's data was considered missing for that entire week and the subject considered a nonresponder. The primary efficacy endpoint will be analyzed using the CMH test controlling for the effect of study center. The presence of a treatment-by-center interaction will be investigated by the Breslow-Day test of homogeneity of odds ratio. The strategy for pooling centers will be based on geographical considerations, with low enrolling centers pooled by geographic region. Details of any pooling performed will be documented prior to database lock and unblinding of the study.

Secondary Endpoints:

For secondary analyses, a subject was considered a monthly responder for a particular month if he/she was a weekly responder for at least 75% of the weeks of a month (at least 3 out of 4 weeks). Secondary endpoints included the following: overall response by gender and age group (<65, >65 years); Rate of responders at least 50% of the weeks (6 out of the 12 weeks); Number of study medication doses taken per week (mean)·Number of rescue bisacodyl doses taken per week (mean); % of subjects not meeting ROME criteria at the end of each treatment week; Time to first BM; % of subjects experiencing a complete/spontaneous BM within 3 hours of each dose; Weekly stool consistency; Number of BMs with straining per week (mean); SBM and CSBM frequency rates during each week (weeks 1 to 12); BM urgency score per week (mean); Bristol Stool Form score per week (mean); Number of BMs per week (mean); Number of diarrhea episodes per week (mean)– diarrhea is defined as >3 watery stools per day; and Weekly stool straining.

Analysis of safety was performed using the Intent to Treat population.

Adverse Events:

Adverse Events were coded using the MedDRA classification to provide a preferred term and primary system organ class for each event. Proportions of subjects with adverse events were presented. Tables of AEs were presented by system organ class and preferred term, and include overall totals for AEs within each system organ class. Counting was done by subject and not by event.

Treatment-emergent AEs were defined as adverse events that had an onset day and time on or after the day and time of the first dose of study drug. Adverse Events having missing onset dates were considered as treatment emergent.

Treatment-emergent AEs were defined as adverse events that had an onset day and time on or after the day and time of the first dose of study drug up to 30 days after the last application of treatment. Adverse Events having missing onset dates were considered as treatment emergent.

The difference in adverse event rates between study groups was tested by Chi-Square or Fisher's exact test with 95% confidence intervals. Adverse events were presented for the overall Treatment Period.

Summary Statistics:

Summary statistics (i.e., mean, minimum, maximum, standard deviation, and number of subjects) were presented for each treatment group for each laboratory parameter at each visit. When calculating the summary statistics only, the last observation within a visit window was used if there were multiple observations. Changes from baseline were presented in a similar format. An additional listing was provided of those subjects who had clinically significant laboratory values. The data were also presented as shift tables and clinically significant abnormalities were examined. Results of laboratory tests for the change from baseline (Screening) and group differences were tested using ANOVA.

Vital Signs:

Summary statistics (i.e., mean, minimum, maximum, standard deviation, and number of subjects) were presented for each treatment group for each vital sign at each visit. When calculating the summary statistics only, the last observation within a visit window was used if there were multiple observations. The data was also presented as shift tables and clinically significant abnormalities were examined. ECG variables were tabulated and presented for data collected at each visit. Data were tabulated and summarized with descriptive statistics (N, mean, SD, CV %, SEM, minimum, and maximum) for each of the ECG variables. The differences in ECG variables between Visit 2 (pre-dose) and Visits 3-5 were tested using ANOVA.

Example 2. Fed v. Fasted Administration of Lactitol

A study was performed to determine the effects of food on absorption of lactitol. Sixteen subjects (8 males and 8 females) were randomized to either Sequence A (fed/fasted) and the other half to Sequence B (fasted/fed) on Day 1 prior to dosing. Subjects returned for Day 8 dosing, 7 days following dose at Day 1, to receive study drug following the opposite food sequence, have pharmacokinetic samples collected and safety procedures performed. A standard dinner was served approximately 6 hours following dose on Day 1 or Day 8. A nighttime snack was permitted, and a standard breakfast and lunch were served prior to discharge from the clinic.

Treatment Period 1:

No food was allowed prior to dosing; water was consumed up to one hour before dosing and then only after one hour after dosing. Subjects assigned to Sequence A (fed/fasted) received a high-calorie and high-fat meal for lunch at 11:30 AM, as described in Table 1. Subjects receiving the high fat high calorie lunch completed the meal within 30 minutes. Dose was administered 30 minutes after the start of the meal. Subjects assigned to Sequence B (fasted/fed) continued to fast prior to dose. The staff mixed the contents of two (2) packets (approximately 21 g) with 8 oz of water. Subjects consumed the dose over 5 to 10 minutes.

Table 1.

| SVG | Unit | Lunch | KCAL | CHO | PRO | FAT |
|---|---|---|---|---|---|---|
| 6 | oz | Beef Lasagna | 299 | 36 | 14 | 11 |
| 1 | cup | Cooked Steamed Carrots | 99 | 16 | 2 | 3 |
| 1 | cup | Side Garden Salad | 62 | 9 | 2 | 2 |
| 1 | oz | Italian Dressing | 84 | 3 | 0 | 8 |
| 1 | ea | Bread Stick | 105.5 | 20 | 3 | 1.5 |
| 1 | ea | Oatmeal Cookie | 168.5 | 25 | 2.5 | 6.5 |
| 12 | oz | Hawaiian Punch | 102 | 25.5 | 0 | 0 |
| | | TOTAL | 920 | 134.5 | 23.5 | 32 |
| | | Caloric Breakdown | | 538 | 94 | 288 |
| | | Meal Composition | | 58% | 10% | 31% |

A standard dinner was served to all subjects approximately 6 hours following dose on Day 1. A nighttime snack was permitted, and a standard breakfast and lunch were served on Day 2 prior to discharge from the clinic.

Doses were administered 30 minutes after the start of the meal. Subjects assigned to Sequence B (fasted/fed) continued to fast prior to dose. The CRU mixed the contents of two (2) packets (approximately 21 g) with 8 oz of water. Subjects consumed the dose over 5 to 10 minutes.

A high-fat (approximately 50 percent of total caloric content of the meal) and high-calorie (approximately 800 to 1000 calories) meal was used. Blood samples were collected prior to dosing and at 10, 20, 30 and 60 minutes (within +/−3 minutes) and then at 2, 4, 6, 8, 10, 12, 16, 18, 20 and 24 hours (within +/−30 minutes) following dose.

An LC-MS/MS method for the determination of lactitol concentrations in human plasma has been successfully developed and validated. The calibration range of the method is 25.0 to 10,000 ng/ml for lactitol using a 50 µl sample aliquot. The results indicate the method is sensitive, selective, accurate, and reproducible.

Results

As shown in FIG. 1, the fasted population (●) showed a rapid rise in lactitol plasma concentrations. By hour 1, the fasted population had average plasma concentrations of 1193 ng/mL plasma and reached a peak concentration of 2412 ng/mL plasma by hour 4. The plasma concentration in the fasted population remained above 1000 ng/mL plasma until hour 8, but the plasma concentration was still far higher than in the fed population (○), 935 v. 387.93, respectively.

FIG. 1 shows that the fed population had a slow increase in lactitol plasma concentrations to a peak concentration of 738.25 ng/mL at hour 4. This peak concentration was more than three times smaller than the peak for the fasted population. In addition, the plasma concentrations in the fed population remained lower than the fasted population from 20 minutes post-dose to hour 12 post-dose (218 ng/mL for fasted v. 124.16 ng/mL for fed).

Furthermore, the AUC for the fed population was 10 times smaller than the AUC for the fasted population. This indicates that less lactitol was bioavailable in the blood of fed subjects as compared to fasted subjects and the total exposure to lactitol is 10 times higher in fasted subjects. The inter-subject variability, as measured by the % of variation (% Coefficient of variation), was lower for the fed condition than for the fasted condition. The % CV values for $C_{max}$, $T_{max}$, $AUC_{0-t}$, and $AUC_{0-\infty}$ ranged from 54.1% to 61.1% for the fasted condition and from 29.4% to 33.9% for the fed condition. The % CV values were similar for the fasted and fed conditions for $\lambda_z$ and $\lambda_{1/2}$, indicating no effect of food on the variability of the elimination rate.

Example 3. Administration of Lactitol in a Constipated Population that Included Elderly A study on administration of lactitol in constipated patients including elderly individuals will be performed. The study will be conducted with similar parameters to Example 1, but for the following modifications.

Approximately 600 male or female constipated adult subjects will be randomized in this study after completing a 14 day screening period to confirm constipation status, with approximately 30% of enrolled subjects having an age greater than 65.

Subjects that meet the BM and Diary Compliance Criteria will be randomized using an automated interactive web response system (IWRS). The randomization schedule will be implemented in the automated interactive web response (IWR) system prior to kit distribution to the site. At the time of randomization the IWRS will assign a drug kit number for site personnel to dispense to the subject. Subjects will be stratified into one of the following two groups:

Group 1: Subjects <65 years of age at time of randomization

Group 2: Subjects >65 years of age at time of randomization.

During Visit 2, subjects will be provided with instructions on how to take the study medication and rescue medication. One bottle of study drug (a 30 day supply) will be dispensed per subject along with one box of rescue bisacodyl. The study drug bottle will be weighed for drug accountability purposes. Subjects will take a daily dose of 2 capfuls of study powder until they return for Visit 3. Subjects will be instructed to return all medication (including bisacodyl) and components at Visit 3.

Treatment Day 1: Starting the morning of Treatment Day 1 (the day after randomization), subjects will measure two (2) capfuls of study medication and ingest it mixed in a beverage of their choice. When possible, subjects should take each dose at approximately the same time every day (preferably in the morning). Subjects that develop persistent diarrhea or loose stools should contact their study center. Subjects with persistent diarrhea or loose stools will be allowed to adjust their dose down to 10.5 g (1 capful) per day.

Subjects will return to the clinic every 4 weeks (+/−2 days) for Visits 3-7. Vital signs (see section 4.1 for details) will be taken. Study personnel will weigh returned study medication bottles and count rescue bisacodyl tablets for accountability purposes and for consistency with the electronic diary reporting. Study personnel must discuss any electronic diary reporting irregularities (e.g. missed study medication or excessive rescue bisacodyl use, reporting compliance). Subjects will be queried for any adverse events or changes to their concomitant medications. Samples for chemistry, hematology and urinalysis will be repeated as outlined in Section 4.1 (Note: serum pregnancy testing will be conducted at Visits 1, 5 and 8 only).

Subjects suspected by the Investigator of having developed lactic acidosis, characterized by abnormally low bicarbonate with abnormally high anion gap (deemed clinically significant by the investigator), should return for a redraw to test for lactate. Subjects with high lactate levels believed to be caused by the study medication should be discontinued.

A 30 day supply of study medication (1 bottle) along with 1 box of rescue bisacodyl will be dispensed at each visit. Unused product will not be redispensed. No rescue medication will be redispensed. Subjects will be instructed to bring all medication (including bisacodyl) and components at each follow up visit.

Subjects that develop persistent diarrhea or loose stools should contact their study center. Subjects with persistent diarrhea or loose stools will be allowed to adjust their dose down to 10.5 g (1 capful) per day.

At Visit 7 (Day 140), 2 bottles of study medication will be dispensed so that subjects have a sufficient supply to reach Visit 8 (Day 180).

Subjects will return at after approximately 180 days of dosing (+4 days) for their final clinic visit. Vital signs will be taken. A 12-lead ECG will be performed by qualified, trained site personnel. ECG output must be reviewed by a physician investigator. A physical examination will be performed. Study personnel will weigh study medication bottles and count rescue bisacodyl tablets for accountability purposes and for consistency with the electronic diary reporting. Study personnel must discuss any electronic diary reporting irregularities (e.g. missed study medication or excessive rescue bisacodyl use, reporting compliance). Subjects will be queried as to whether the study medication was taken with food. Subjects will also be queried for any adverse events or changes to their concomitant medications. Samples for chemistry, hematology and urinalysis will be repeated. Subjects suspected by the Investigator of having developed lactic acidosis (as described in Section 4.3.3) should return for a redraw to test for lactate.

At Day 194, approximately 2 weeks after the last study visit or early term visit, site personnel will contact subjects by telephone to query if any new adverse events have occurred and if any adverse events ongoing at Visit 8 have resolved. Subjects will also be asked about the status of their concomitant medications.

Example 4. Administration of Lactitol for One Year

This is an open-label, multi-center study in which constipated subjects will receive the formulation for 12 months. The study set up is similar to Example 1.

Approximately 300 constipated subjects will be enrolled into this study, including approximately 100 elderly subjects (>65 years of age at Visit 1). Qualifying subjects will receive the formulation at Visit 1 and will begin a 12-month Treatment Period. Subjects will return for clinic visits at the end of Months 2, 4, 6, 9 and 12. A follow up call will take place 2 weeks after the end of treatment. A completed subject is defined as a subject that completes the Visit 6 (Month 12) visit.

The formulation will be provided polyethylene bottles containing sufficient study medication for 30 days of dosing. The bottles will be equipped with a cap that can be used to measure 10.5 grams of the formulation. Each bottle will also have a clinical label containing a caution statement, study code, study sponsor and subject number. Subjects will be instructed to mix the contents of 2 capfuls (approximately 21 g) in 4-8 oz of juice or other beverage, and take once daily preferably in the morning. Subjects that develop persistent diarrhea or loose stools will be allowed to adjust their dose down to 10.5 g (1 capful) per day.

Treatment Day 1:

Starting on the morning of Treatment Day 1 (the day after Visit 1), subjects will measure 2 capfuls of study medication and ingest it mixed in a beverage of their choice. Subject will take a daily dose of 2 capfuls until they return for Visit 2. Subjects that develop persistent diarrhea or loose stools should contact their study center. These subjects will be allowed to adjust their dose down to 10.5 g (1 capful) per day.

Subjects will continue to take the formulation daily and will return to the clinic for Visits (Days 60, 120, 180, 270 and 360). Visit 3 will occur on Day 120. At each visit, vital signs and ECGs will be recorded. Study personnel will weigh returned bottles and count rescue bisacodyl for accountability purposes. Subjects will be queried for any adverse events or changes to their concomitant medications. Subjects will complete the PAC-QOL and PAC-SYM questionnaires. Samples for chemistry, hematology and urinalysis will be repeated. Subjects will be dispensed 2 new bottles of study medication. Subjects will be instructed to return all bottles and bisacodyl at the next follow up visit.

At the final visit (Day 360), vital signs, ECGs, and a physical examination will be performed. Study personnel will weigh returned bottles and count bisacodyl for accountability purposes. Subjects will be queried as to whether the study medication was taken with food. Subjects will also be queried for any adverse events or changes to their concomitant medications. Subjects will complete the PAC-QOL and PAC-SYM questionnaires. Samples for chemistry, hematology and urinalysis will be repeated. Clinically significant laboratory abnormalities present should be followed until resolved or are considered stable.

At Day 374, approximately 2 weeks after the last study visit or early term visit, site personnel will contact subjects by telephone to query if any new adverse events have occurred and if any adverse events ongoing at Visit 6 have resolved. Subjects will also be asked about the status of their concomitant medications.

What is claimed:

1. A method of reducing plasma concentration of lactitol in a subject, the method comprising administering a total dose of an effective amount of a formulation comprising lactitol after the subject has consumed a meal, wherein the meal is a high fat meal.

2. The method of claim 1, wherein the meal is a high calorie meal.

3. The method of claim 2, wherein the high calorie meal comprises at least about 500 calories.

4. The method of claim 2, wherein about 50% of the calories in the high calorie meal are attributable to fat.

5. The method of claim 1, wherein the formulation is administered as a powder.

6. The method of claim 5, wherein the formulation is administered as the powder reconstituted in a solution.

7. The method of claim 1, wherein the effective amount of lactitol comprises from about 5.0 grams to about 30 grams.

8. The method of claim 1, wherein the effective amount of lactitol comprises from about 10.0 grams to about 25 grams.

9. The method of claim 1, wherein the effective amount of lactitol comprises about 21.0 grams.

10. The method of claim 1, wherein the effective amount is divided into two or more doses.

11. The method of claim 1, wherein the effective amount is divided into two doses.

12. The method of claim 6, wherein the solution is selected from the group consisting of juice, soda, water, and balanced electrolyte solution.

13. The method of claim 1, wherein the formulation is a liquid.

14. The method of claim 13, wherein the formulation comprises one or more of natural flavoring, artificial flavoring, or preservatives.

15. The method of claim 1, wherein the formulation is a tablet.

16. The method of claim 1 further comprising administering an agent selected from the group consisting of polyethylene glycol, sulfate salts, magnesium salts, stimulant laxatives, and lubiprostone.

17. The method of claim 16, wherein the osmotic agent is lubiprostone.

18. The method of claim 1, wherein the subject has three or more spontaneous bowel movements.

19. The method of claim 18, wherein the spontaneous bowel movements occur within a seven day period.

20. The method of claim 1, wherein the formulation is provided in bulk.

21. The method of claim 1, wherein the subject has a plasma concentration of lactitol of less than 1000 ng/mL four hours after administration of the effective amount of lactitol.

* * * * *